United States Patent [19]
Edwards et al.

[11] Patent Number: 5,510,081
[45] Date of Patent: Apr. 23, 1996

[54] TEST SAMPLING APPARATUS

[75] Inventors: John Edwards, Jindalee, Australia; David Nuske, Denmead, United Kingdom

[73] Assignee: Queensland University of Technology, Brisbane, Australia

[21] Appl. No.: 315,845

[22] Filed: Sep. 30, 1994

Related U.S. Application Data

[63] Continuation of Ser. No. 976,209, Nov. 13, 1992, abandoned.

[30] Foreign Application Priority Data

Nov. 13, 1991 [AU] Australia .................................. PK9497

[51] Int. Cl.⁶ ........................................................ G01N 35/10
[52] U.S. Cl. .............................. 422/63; 422/65; 422/102; 422/104
[58] Field of Search ................................ 422/50, 63, 68.1, 422/99, 102, 104, 56, 58, 65; 435/294, 295

[56] References Cited

U.S. PATENT DOCUMENTS

| | | | |
|---|---|---|---|
| 4,022,579 | 5/1977 | Revillet et al. | 422/65 |
| 4,157,895 | 6/1979 | Finlay et al. | 422/56 |
| 4,391,774 | 7/1983 | Dupain | 422/50 |
| 4,882,127 | 11/1989 | Rosenthal et al. | 422/50 |
| 5,055,263 | 10/1991 | Meltzer | 422/104 |
| 5,094,816 | 3/1992 | Ishizaka | 422/56 |
| 5,206,171 | 4/1993 | Dillon et al. | 422/63 |

*Primary Examiner*—Michael G. Wityshyn
*Assistant Examiner*—Rachel Heather Freed
*Attorney, Agent, or Firm*—Edwin D. Schindler

[57] ABSTRACT

A distribution apparatus for transporting an article struck from sheet metal is disclosed, which includes a receiving head having a recess for receiving the article struck from the sheet. The recess includes a resilient interference feature extending inwardly beyond the boundary of the article to be received. Transporting apparatus is further provided for transporting the receiving head to a selected destination and, finally, a discharging element is included for discharging the article from the receiving head at the selected destination.

15 Claims, 9 Drawing Sheets

TEST SAMPLING APPARATUS

This is a continuation of application Ser. No. 07/976,209, filed Nov. 13, 1992, now abandoned.

This invention relates to distribution apparatus.

This invention has particular but not exclusive application to distribution apparatus adapted to place pieces of paper card impregnated or smeared with blood into selected containers and for illustrative purposes reference will be made to such application. However, it is to be understood that this invention could be used in other applications, such as the distribution of pieces of paper card smeared with other dried liquids or, for example, the distribution of pressed sheet metal components into selected locations of an assembly plant.

Many medical tests are conducted using test samples of blood taken from patients. The test samples may comprise dry blood retained on a piece of paper card labeled with the patients particulars. Preferably the blood sample covers at least the area bounded by a test circle or a plurality of test circles marked on the card. For testing purposes, portions of the card smeared or impregnated with blood are subsequently placed in containers containing selected reactants.

Distribution apparatus adapted to punch four circularly shaped samples from the area bounded by a test circle and to subsequently place each test sample in a selected container are known. Typically the apparatus includes one or more transporters adapted for movement in opposing directions and four tubular shaped head portions each adapted to receive therein a single test sample and wherein the samples are selectively retained within each head portion by vacuum forces. Unfortunately the process of punching test samples from a piece of paper card often results in the generation of small fragments of paper which may collect in the head portions and as a consequence effect the ability of the apparatus to create or maintain a vacuum within each respective head portion. This leads to unreliable operation.

Typically up to four different tests may be conducted each requiring a sample of the patient's blood. When taking blood samples from a patient, it is not possible to determine the number of tests which will be conducted. Preferably, the patient's card is smeared with enough blood sufficient to conduct twelve tests. Unfortunately the apparatus described above does not include means by which a user may control or select the number of test samples punched from the paper card and as a consequence thereby minimize any wastage of blood samples.

The present invention aims to alleviate at least one of the above disadvantages and to provide distribution apparatus which will be reliable and efficient in use. Other advantages of this invention will hereinafter become apparent.

With the foregoing in view, this invention in one aspect resides broadly in transporting apparatus for transporting an article struck from sheet material, including:

a receiving head having a recess for receiving the article struck from the sheet;

the recess including resilient interference means extending inwardly beyond the boundary of the article to be received;

transporting means for transporting the receiving head to a selected destination, and discharge means for discharging the article from the receiving head at a selected location.

The resilient interference means may be formed as internal splines or the like or an internal resilient liner within a rigid housing. Preferably however the receiving head or gripping member is formed of resilient material and the recess has an inner boundary extending inwardly beyond the boundary of the article to be received. Alternatively if the article being struck and/or the punch is of a suitable resilient nature the interference means may be of a non-resilient form. The transportation apparatus is suitably adapted for receiving a blood spot sample and the receiving head is formed from a polyurethane preferably having a hardness of 90 shore A durometer hardness.

Suitably the blood spot sample is struck from a blood impregnated card by an axially advanced cylindrical die or punch and the recess is formed by moulding the receiving head about a corresponding cylindrical pin. Preferably the diameter of the recess is smaller than the diameter of the die and the sample.

The discharge means may be an air blast or the like but preferably it comprises a plunger supported for movement into the recess to displace a retained article from the recess.

The transportation means may include a conveyor belt or similar arrangement adapted to transport the receiving head. Preferably the transportation means includes a transporter or a plurality of transporters capable of movement in a single direction or a plurality of directions and may constrain the receiving head for movement along rails or tracks. Furthermore, each transporter may be mechanically driven and powered by a pneumatic or an electric motor.

In another aspect, this invention resides broadly in test sampling apparatus including:

holding means for holding an array of test containers;

retaining means for retaining a card from which test samples are to be taken;

production means for producing test samples from the card retained by the retaining means;

transportation apparatus for transporting the test sample to a selected test container and including retention means for selectively retaining a produced test sample.

The test sampling apparatus may include actuation means adapted to control the transportation apparatus and the selected retention of test samples. The actuation means may also control the number and size of test samples produced by the production means. Preferably the actuation means is a computer which may be programed to produce a desired number of articles each of which may be subsequently deposited in a preselected location.

Preferably, the retention means includes a head portion or gripping member adapted to frictionally receive an article and disengagement means associated with the head portion for stripping the article from the head portion. The transportation apparatus may be of the type defined above which incorporates resilient retaining means for retaining the test sample. Alternatively the retention means may employ a vacuum or electrostatic or magnetic forces of attraction to hold the article to the transporter, or mechanical means adapted to grasp the article such as a plurality of jaws.

In a preferred form the production means includes punching means and the receiving head receives test samples struck from the punching means. Centering or locating means in the form of an abutment may be provided for centering the receiving head relative to the punching means whereby the recess is operatively aligned with the punching means to receive the struck test sample. Alternatively, electronic centering means may be utilised.

The test sampling apparatus may include production means for producing a plurality of test samples. Preferably the number of samples and the size of the samples produced by the production means may be selectively varied.

The test samples may include samples of dry blood carried on paper card produced from a larger sheet of paper card using a punch. Preferably the apparatus includes a plurality of punches and control means for controlling the number of articles produced. The punches may be constituted by a punch and a die set and the punch may be adapted to enter the recess so as to expand the innermost boundaries thereof and simultaneously advance the struck sample into the recess whereby the innermost boundaries will contract upon withdrawal of the punch from the recess and clamp about the blood spot sample therein. In one embodiment, the control means may be adapted to disable or otherwise prevent the engagement of selected punches and the paper card.

It will be appreciated that blood smeared on the paper card may not always cover the test circle. Accordingly, the relative position of each punch or the sample card may be adjustable. Furthermore, the apparatus may include scanning means for scanning the shape of the blood spot and for subsequently positioning the punches or the card such that the test samples each contain a minimum area of blood.

In yet a further aspect this invention resides broadly in a punch and die set assembly including:

a plurality of punches supported for reciprocal movement about spaced parallel axes, each said punch having a punching end and a following end;

a plunger assembly including a plunger member having columns adapted to abut the following ends of said punches, said plunger member having a series of columns combinations and each combination being adapted to abut a selected said following ends, and alignment means for operatively aligning a selected one of said series of columns with said following ends.

BRIEF DESCRIPTION OF THE DRAWINGS

Figure 1:
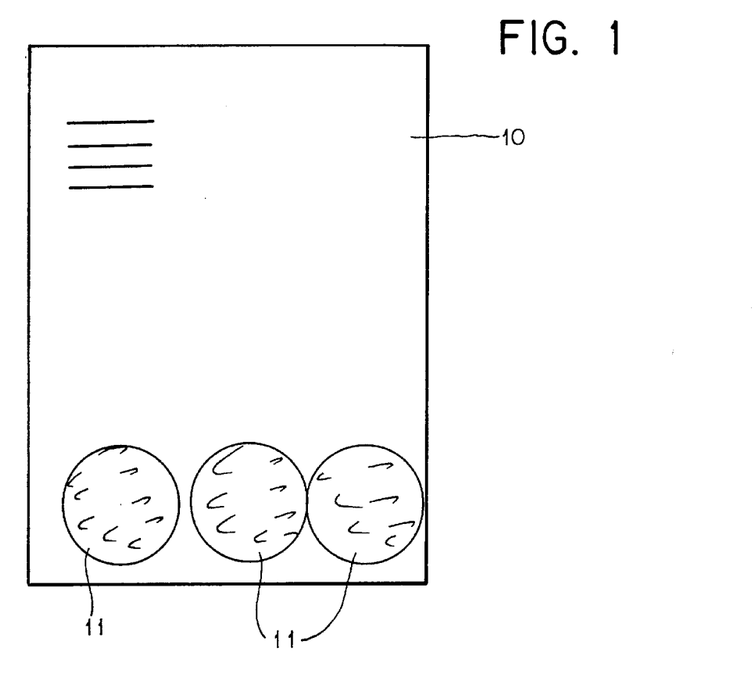
FIG. 1 is a plan view of a piece of paper card on which there is smeared samples of a patient's blood.

In order that this invention may be more easily understood and put into practical effect, reference will now be made to the accompanying drawings which illustrate a preferred embodiment of the invention, wherein:

FIG. 1 illustrates a typical sheet of paper card 10 on which there is recorded a patient's particulars and three test circles 11 each covered with a dried sample of the patient's blood.

Figure 2:
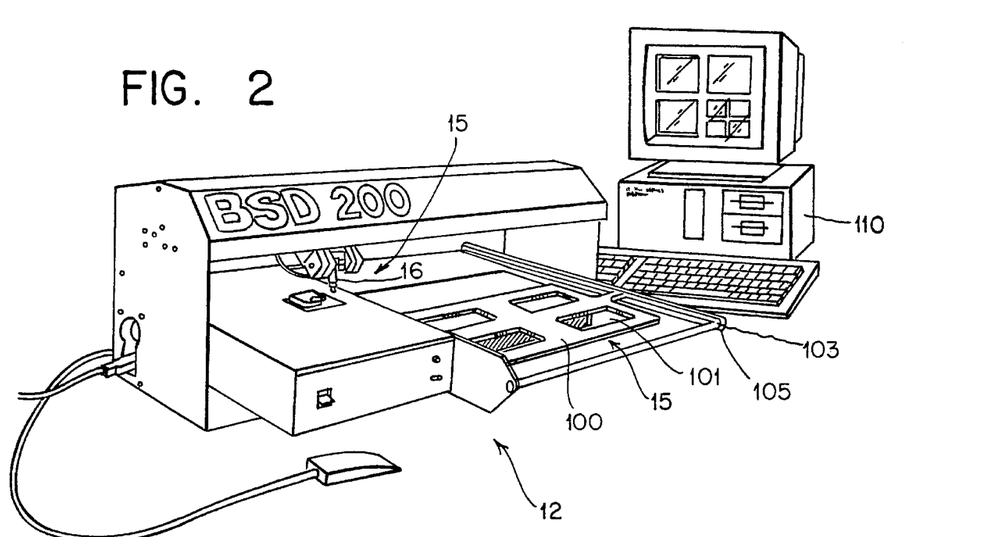
FIG. 2 is a perspective view of distribution apparatus constructed in accordance with the present invention.

The present invention relates to distribution apparatus 12 including production means including a punch assembly 13 for the production of blood stained test samples of paper card 14 punched from test circles 11 of the type illustrated in FIG. 1, and transportation means 15 including a transporter 16 for selectively depositing the test samples 14 into pre-selected containers 17.

Figure 3:
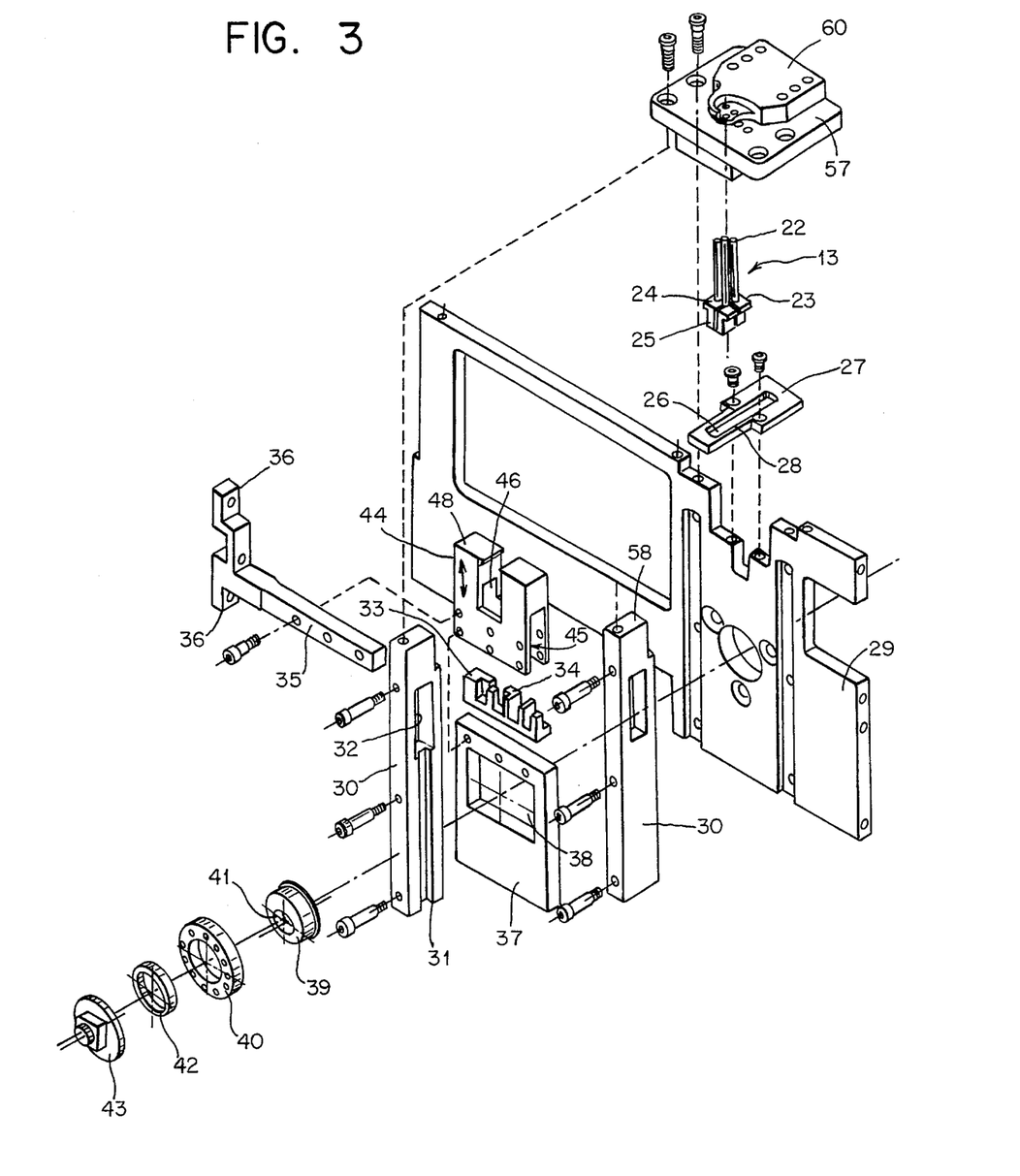
FIG. 3 is a perspective view in line for assembly of production means for producing test samples constructed in accordance with the present invention.

The punch assembly 13 includes four cylindrical pins or punches 22 each mounted on a separate "L" shaped base member 23 comprising a base plate 24 and a dependent flange 25. The four punches are grouped together such that the abutting flanges 25 form a prism which is slidably located in and extends below a slot 26 formed in an end portion of a plate like lower punch stop 27 and wherein the edges of the base plate 24 may rest upon the wall 28 surrounding the slot 26.

The lower punch stop 27 is mounted on a supporting wall 29 intermediate two upstanding guide members 30 also mounted thereto. The guide members 30 each include a vertically oriented channel 31 which communicates with a vertically oriented slot 32 and wherein the channels 31 and the slots 32 are aligned.

The punch assembly 21 also includes a punch selector assembly including a punch selecting block or punch selector 33 having a plurality of columns 34 of equal height and differing shape. The columns 34 are intended to engage or abut the dependant flanges 25 of selected base plates 24 such that selected combinations of one to four punches 22 may be selectively advanced. Accordingly, the shape of the various columns 34 and their arrangement on the punch selector 33 is directed towards this purpose.

The punch selector 33 is slidably mounted on a supporting arm 35 having mounting flanges 36 for the mounting of the arm to or punch selector motor, not shown. The punch selector 33 is operatively connected to the output shaft of the punch selector motor which controls the advancement of the punch selector along the length of the supporting arm 35.

The punch selector 33 and the supporting arm 35 extend through opposed slots 32 and may move within the slots 32 in a vertical direction when driven by a plate like ram 37 slidably retained within the channels 31. The ram 37 includes a square shaped aperture 38 in which there is located a cylindrically shaped member 39 rotatably mounted within a bearing 40. The cylindrically shaped member 39 having an eccentrically located aperture 41 which is connected to the output shaft of an electric motor or ram motor, not shown, and wherein the bearing 40 and the cylindrical member are maintained in a working relationship by a bearing collar 42 and a locking collar 43.

The supporting arm 35 and an upper portion of the ram 37 are each attached to a punch return 44 having a lower longitudinal passageway 45 through which the punch selector 33 slidably extends, and an upper, intersecting transverse passageway 46 through which the slotted end portion of the lower punch stop 27 extends. Located above the transverse passageway 46 are two inwardly directed flanges or stops 48 which are separated by a gap through which the punches 22 extend.

Figure 4:
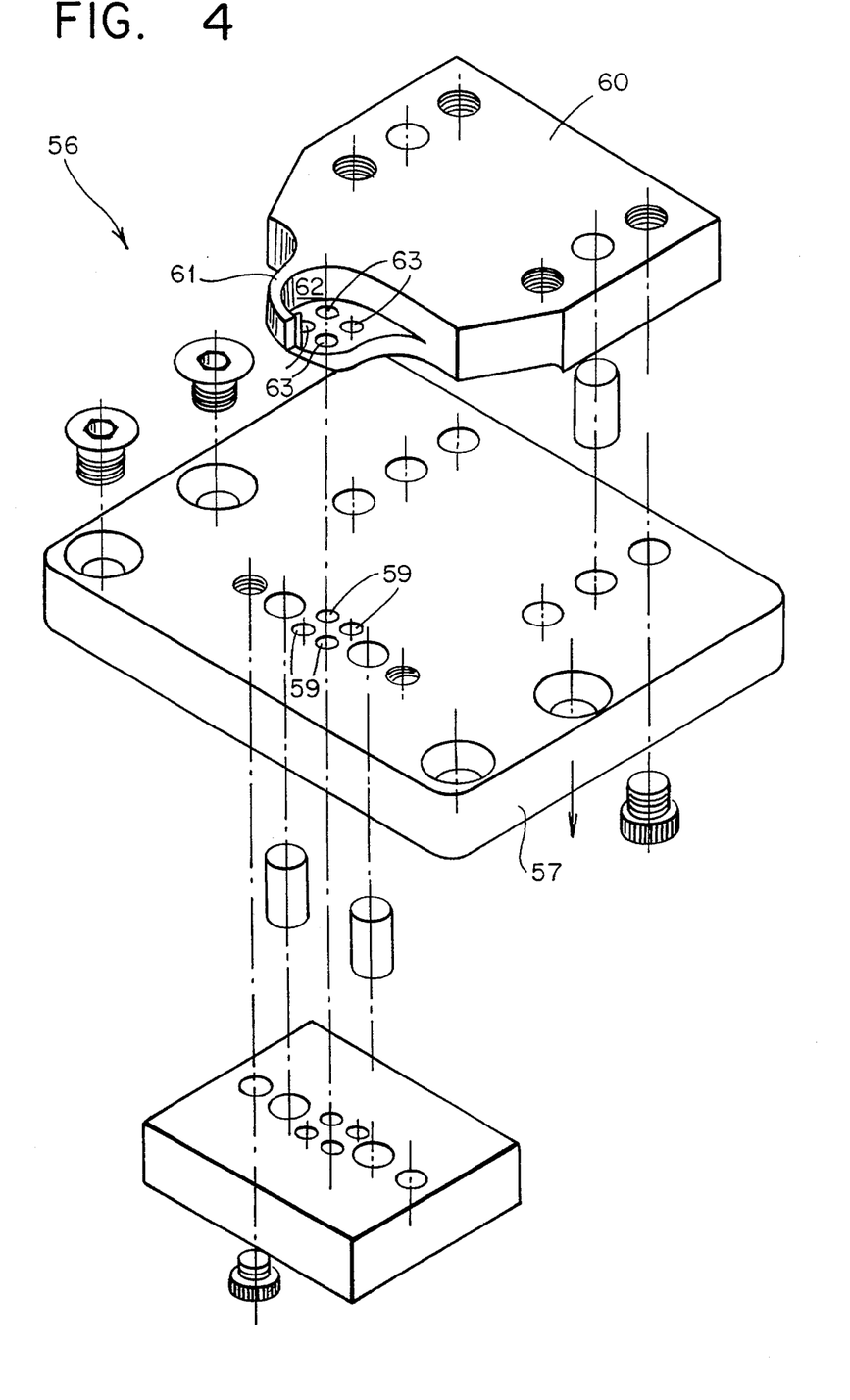
FIG. 4 is a detailed perspective view in line for assembly of a card holder assembly constructed in accordance with the present invention.

The distribution apparatus further includes a card holder assembly 56 adapted to hold and locate a paper card 10 smeared with blood relative to the punches 20 located below. The card holder assembly 56 includes a base plate 57 mounted on the upper ends 58 of respective guide members 30 and wherein the base plate 57 includes four lower punch apertures 59 through which a respective punch 20 nay extend.

The card holder assembly 56 also includes a transporter locating plate 60 mounted on the base plate 57 and having a locating portion 61 spaced above the base plate and between which a user may insert a paper card 10. The locating portion 61 includes an arcuate wall 62 against which a lower portion of the transporter 16 may abut and four upper punch apertures 63.

Figure 5:
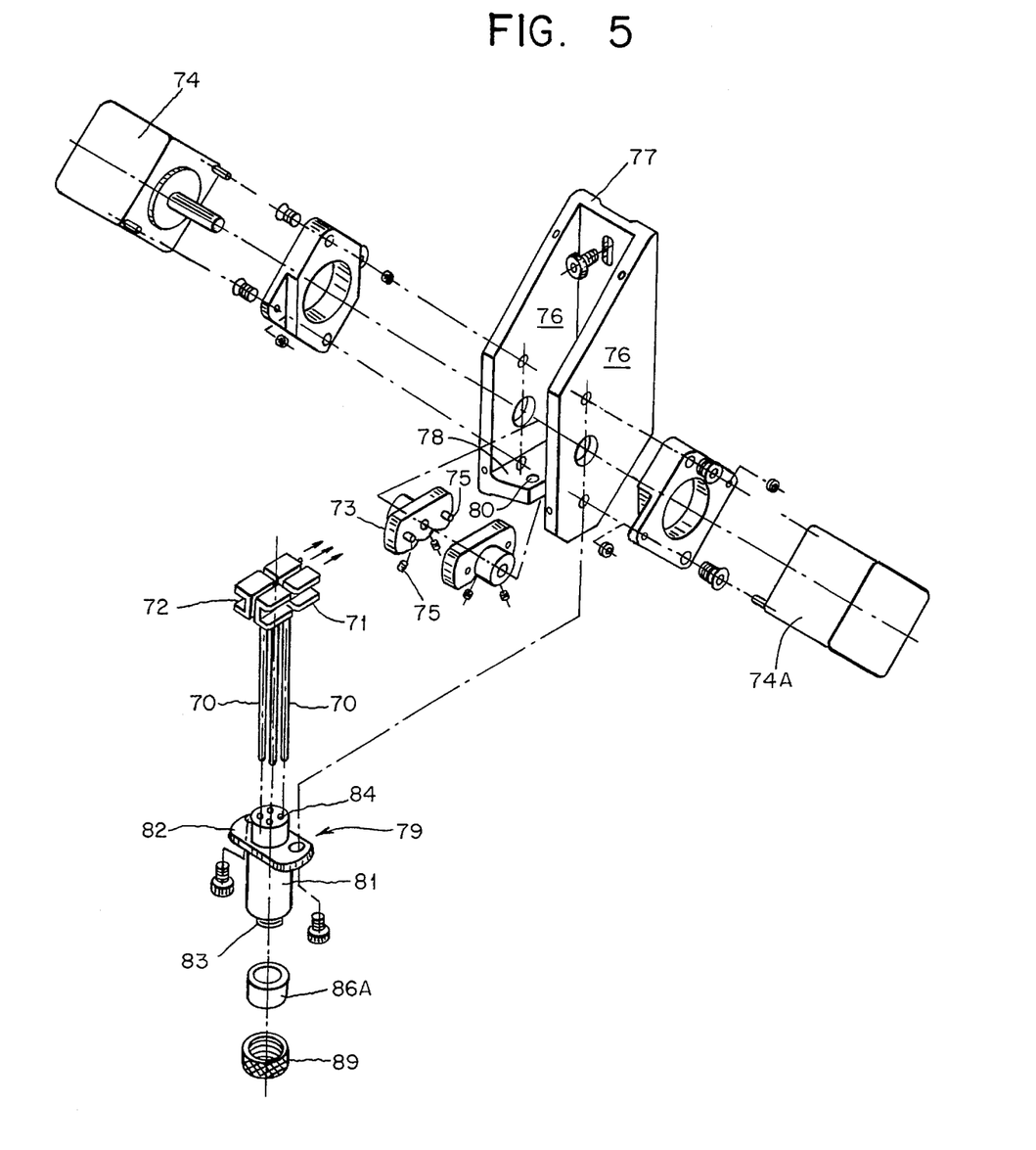
FIG. 5 is a perspective view in line for assembly of a gripping assembly constructed in accordance with the present invention.

The transporter 16 includes four stripping pins 70 each dependant from a respective pin mounting 71 having a laterally extending channel 72. The pins 70 are mounted between opposed rocker assemblies each having a rocking plate 73 mounted on an output shaft of a respective electric motor 74 and 74A. The rocking plates 73 each include two pegs 75 which extend outwardly therefrom and which slidably engage within a channel 72 of an adjacent pin mounting 71.

The electric motors 74 and 74A are mounted on opposing walls 76 of a channel shaped, motor mounting bracket 77 having lower inwardly directed mounting flanges 78 for the mounting thereto of a gripper assembly 79 and upper pin apertures 80 through which respective pins 71 extend.

The gripper assembly 79 includes a substantially cylindrical body portion 81 having mounting arms 82 for attachment to mounting flanges 78, a threaded end portion 83 and four downwardly extending pin receiving bores 84.

Figure 6:
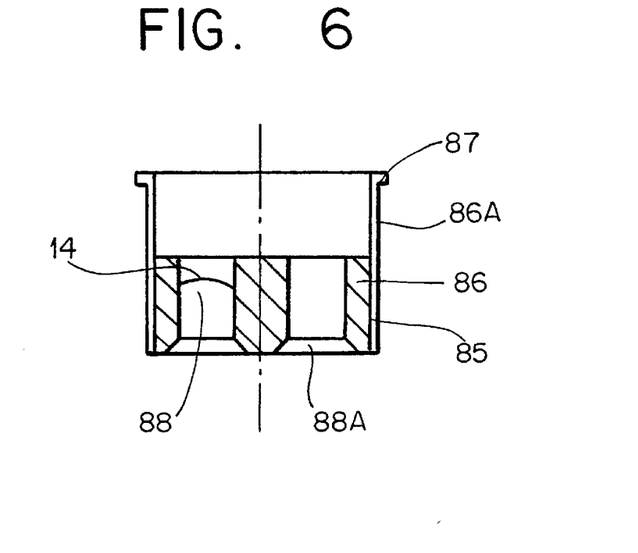
FIG. 6 is a cross-sectional view of gripping member constructed in accordance with the present invention.

The gripper assembly 79 also includes a resilient gripping member 85 manufactured from polyurethane having a cylindrical body portion 86 and retained within a cylindrical metal sleeve 86A having an upper peripheral flange 87. The body portion 86 includes four sample receiving bores 88 each having a tapered entry 88A for guiding misaligned punches into the respective bores 88 and wherein the diameter of the bores 88 are smaller than the diameter of the punches 22 and the test samples to be received therein.

The gripping member 85 is releasably secured to the threaded end 83 by a looking nut 89 having a lower annular flange against which flange 87 may abut and through which the body portion 86 may extend.

The pins 70 extend through respective aligned bores 84 and 88 and wherein the diameter of the pins 70 is smaller than the diameter of the bores 84 and the bores 88.

Figure 7:
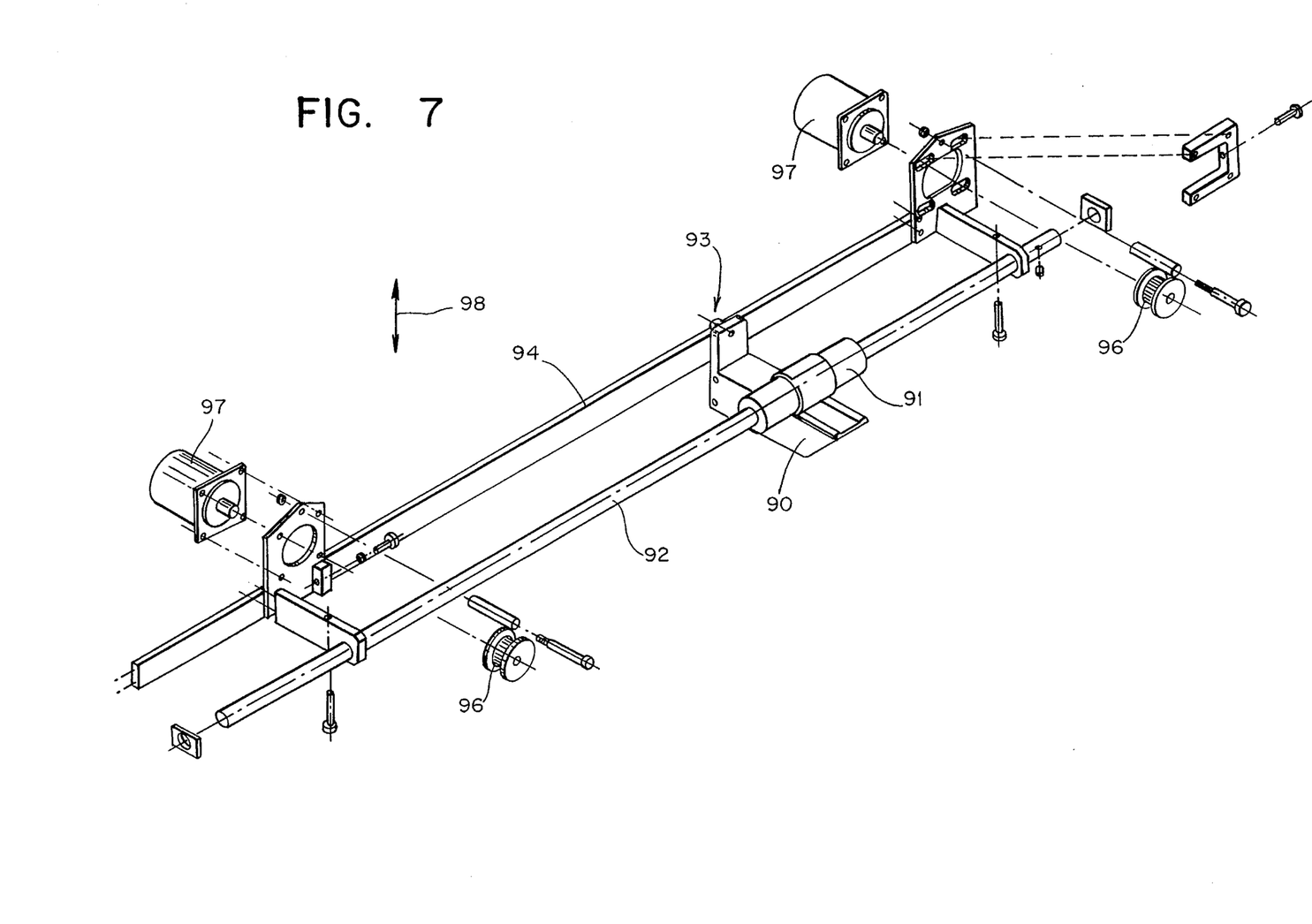
FIG. 7 is a perspective view in line for assembly of an X axis assembly constructed in accordance with the present invention.
Figure 8:
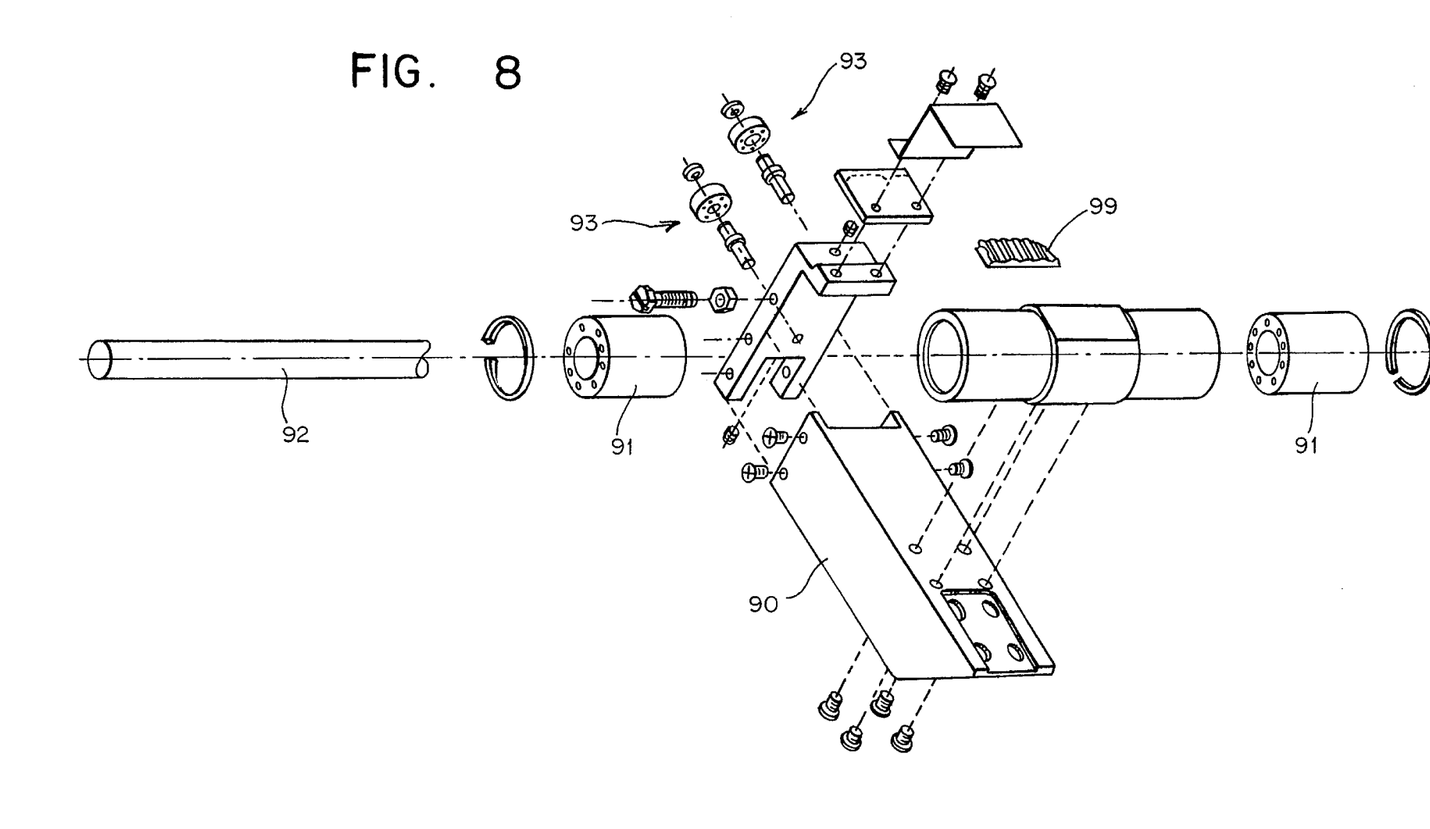
FIG. 8 is a detailed perspective view in line for assembly of the X axis assembly illustrated in FIG. 7.

The transporter 16 is mounted on a mounting arm 90 having a bearing 91 slidably mounted on a horizontally orientated guide rod 92 and opposing upper and lower roller assemblies 93 which are free to roll along the upper and lower edges of an adjacent supporting guide rail. Movement of the transporter 16 in a horizontal direction 95, i.e. along an X axis, is assisted by a belt 99, shown in section, the ends of which are attached to opposing sides of the transporter 16, and wherein the belt is suspended between two opposing sprockets 96 each mounted on the output shaft of a respective electric motor 97 mounted on opposing ends of the guide rail 94.

Figure 9:
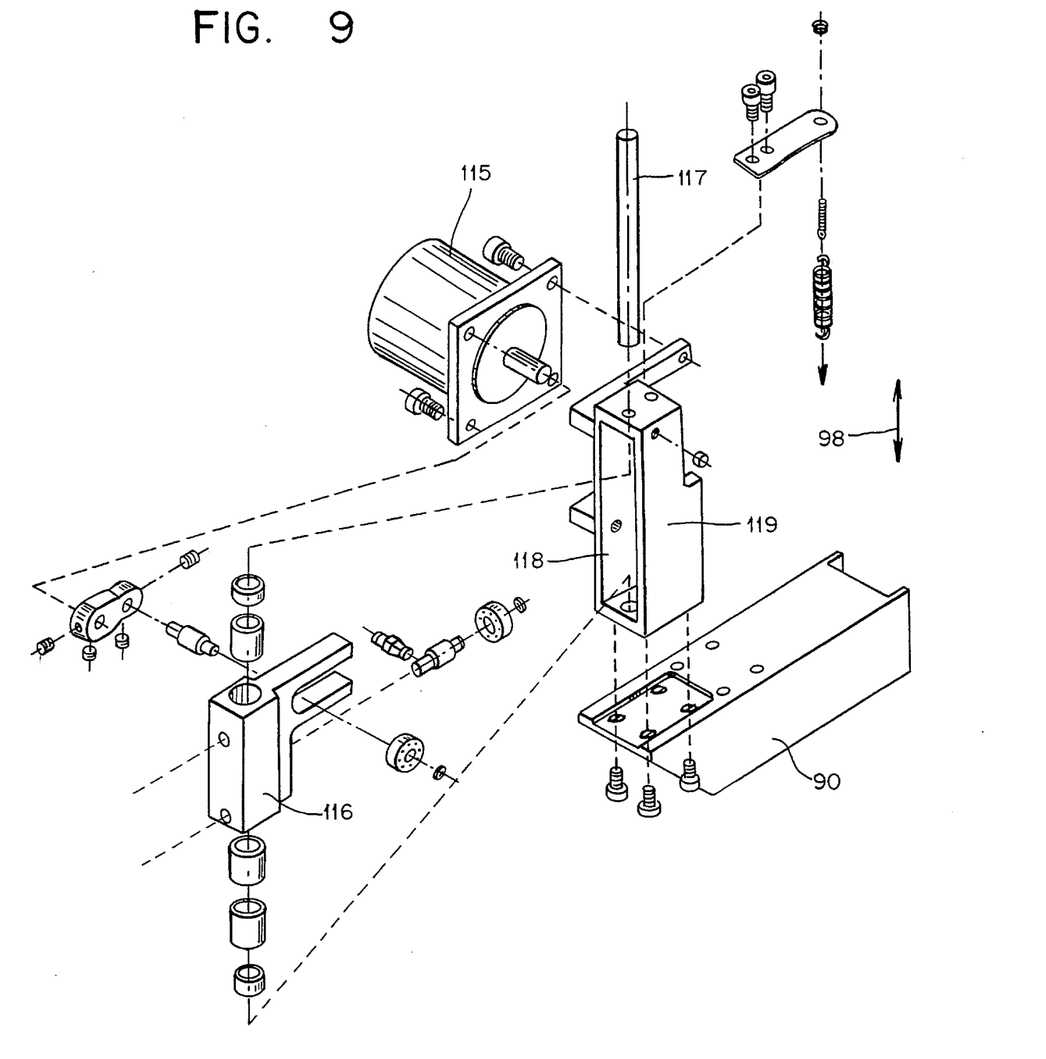
FIG. 9 is a perspective view in line for assembly of a Z axis assembly constructed in accordance with the present invention.

The transporter 16 may also move in a vertical direction 98, i.e. along a "Z" axis, and wherein movement is effected by a "Z" axis electric motor 115 which controls the vertical movement of a transporter mounting bracket 116 along a shaft 117 mounted within a slotted passageway 118 of a "Z" axis motor mounting bracket 119. The motor mounting bracket 77 supporting the gripper assembly 79 is attached to the transporter mounting bracket 116.

Figure 10:
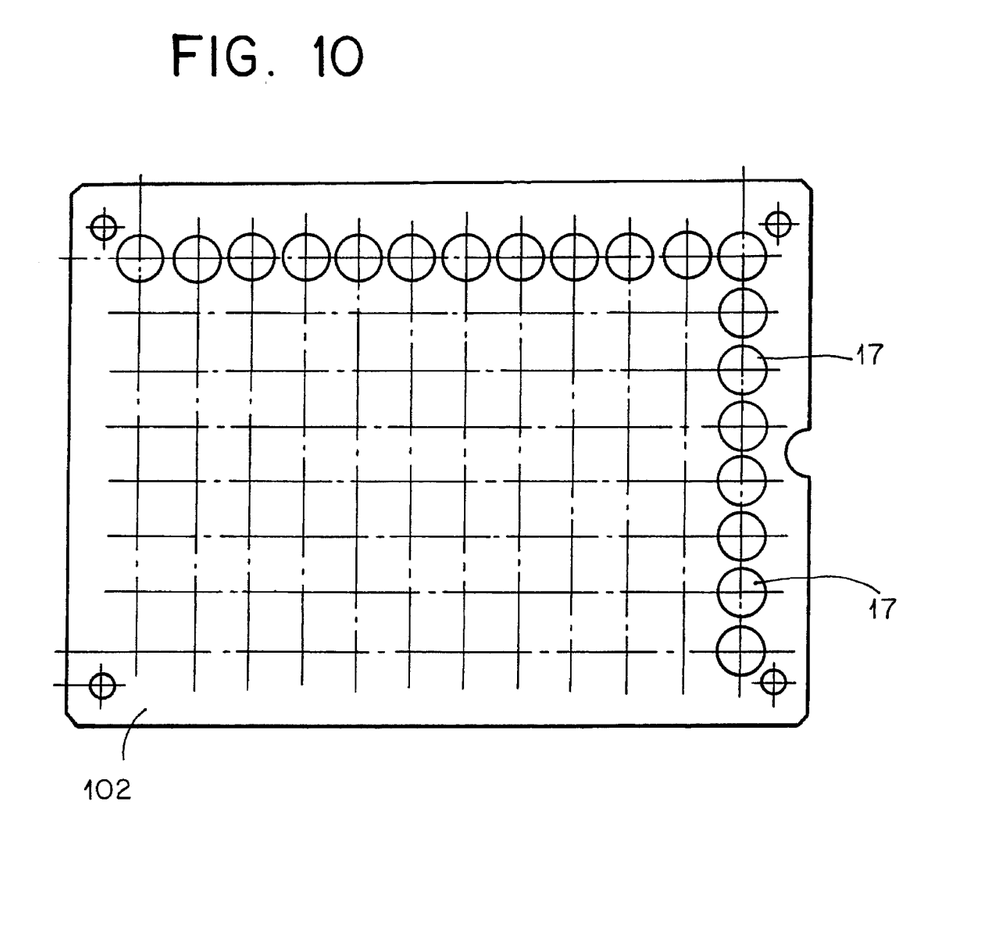
FIG. 10 is a plan view of a tray adapted to hold a plurality of containers.

The distribution apparatus 12 also includes a table assembly including a table top 100 having a plurality of rectangular tray receiving apertures 101 in which selected trays 102 having a desired number and configuration of containers 17 may be located. However, it will be appreciated that trays other than the tray 102 illustrated in FIG. 10 may be used in connection with the distribution apparatus. For example, the table top 100 may include a plurality of upstanding posts to which respective corners of an "AGAR" tray may be releasably secured. Alternatively, the table top 100 may be configured to support one or more microtiter trays, trays having an array of dimples formed therein, or trays in the form of a rack adapted to support a plurality of test tubes. The trays may locate within the tray receiving apertures, or be supported by the table top 100 and/or supporting posts or the like extending upwardly therefrom.

Figure 11:
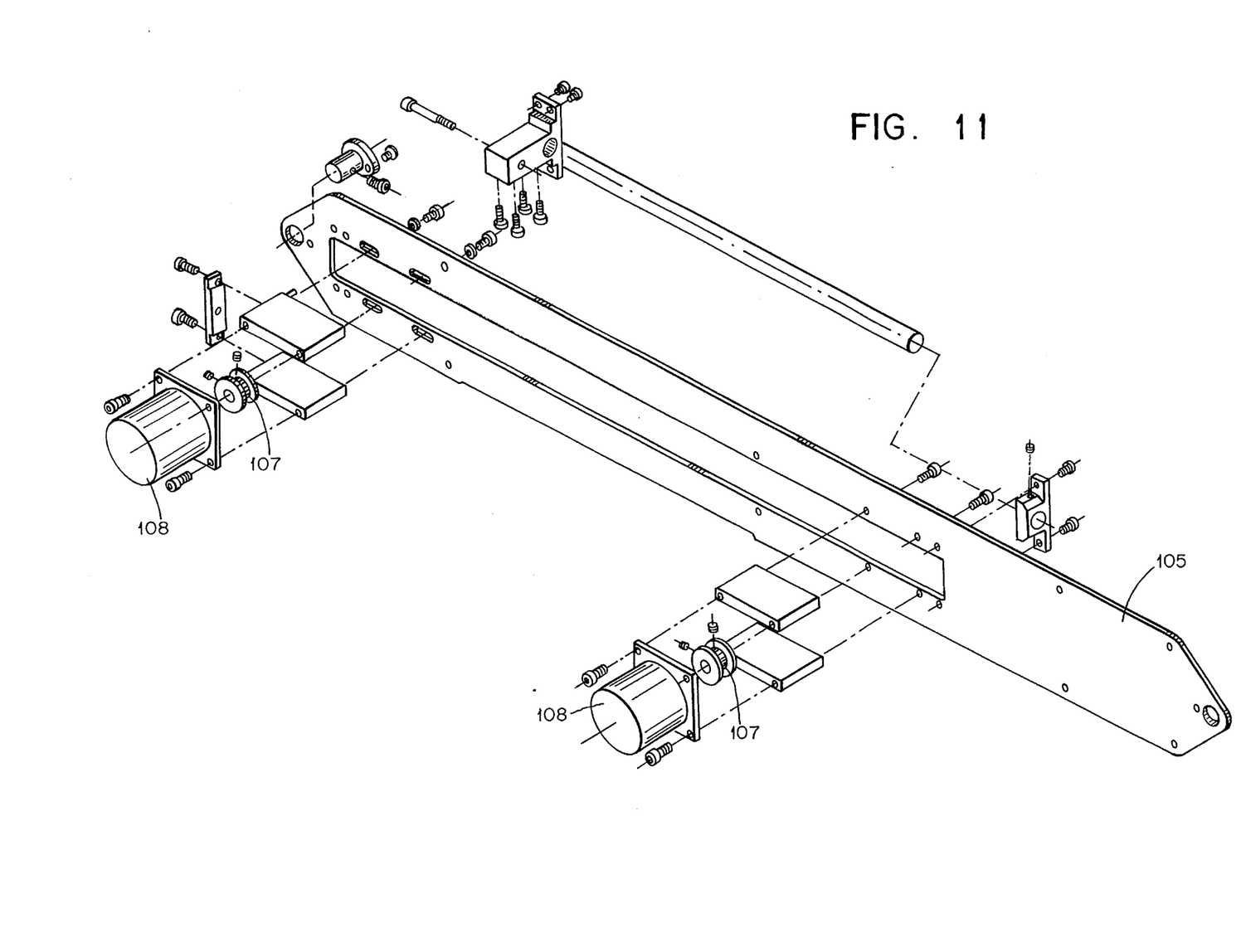
FIG. 11 is a perspective view in line for assembly of a Y axis assembly constructed in accordance with the present invention.

The table top 100 is supported by outwardly extending arm members 103 having roller assemblies mounted thereon and which are free to roll within respective channel shaped table guide members 105.

Movement of the table top 100 in a horizontal direction 106 transverse to the direction of horizontal movement of the transporter 16, i.e. along a Y axis, is assisted by a belt, not shown, the ends of which are attached to opposing sides of the table top 100, and wherein the belt is suspended between two opposing sprockets 107 each mounted on the output shaft of a respective electric motor 108 mounted on opposing ends of the guide member 105.

A standard computer 110 programmed with specific software may be used to actuate the various electric motors and as a consequence, the number of test samples 14 punched from a piece of paper card 10 and the subsequent placement of those samples in selected containers. The computer may also be used to selectively control the number and configuration of test samples 14 punched from a piece of paper card 10.

In use, a paper card 10 may be inserted between the base plate 57 and the transporter locating plate 60 such that the test circle 11 smeared with the patient's blood is positioned directly above the four lower punch apertures 59.

The user, may, using the computer 110, select the particular arrangement of test samples to be produced by the punch assembly 21 from the nine possible combinations available, i.e. combinations of one to four test samples 14, details of the trays being used, and the location of the containers into which each test sample is to be deposited.

As a consequence of the data programmed into the computer 110, the punch selector motor, which controls the positioning of the punch selector 33, will locate the particular portion of the punch selector 33 which corresponds to the desired arrangement of test samples directly below the base members 23 of the punches 22.

Having completed the positioning of the punch selector 33, the user may actuate the ram motor using a foot operated switch, not shown, thereby effecting the reciprocal movement of the ram 37 in a vertical direction. The resulting engagement of the columns 34 of the punch selector 33 with selected aligned base members 23, due to the upward movement of the ram 37, causes the advancement of the head portions of the corresponding punches 22 into respective aligned sample receiving bores 88 beyond a start position within their respective lower punch apertures 59. The upward movement of the punches 22 causes a correspondingly shaped test sample 14 to be punched from the paper card 10 and subsequently frictionally retained within a respective sample receiving bore 88.

The retraction of the punches 22 from respective sample receiving bores 88 is effected by the downward movement of the punch return 44 and the engagement of stops 48 with adjacent base plates 24.

Once the punches 22 have been removed from the sample receiving bores 88, the computer may direct the upward movement of the transporter 16 along the Z axis, the horizontal movement of the transporter 16 along the X axis, and movement of the table top 100 such that a test sample 14 is located directly above the particular container 17 into which it is to be deposited.

The deposit of test samples 14 into selected containers 17 is achieved automatically by the actuation by the computer 110 of electric motors 74 or 74A, which when operated in either a forward or reverse direction cause the downward movement of selected pegs 75 and the extension of an associated pin 71 through an aligned sample receiving bore 88 thereby discharging the test sample 14 retained therein. In order reduce the velocity at which the test sample 14 strikes the base wall of the container 17, and accordingly avoid the possibility of the test sample bouncing out of the container, the transporter 16 may be moved downwardly such that the gripper assembly is closer to the selected container.

The process is repeated until all of the test samples 17 held by the gripper assembly 79 have been deposited into containers 17.

Once all of the test samples 17 have been discharged from the gripper assembly 79, the transporter is returned to its initial position wherein the lower portion of 86 of the gripping member 85 is located in the locating portion 61 such that the sample receiving bores 88 and the punch apertures 59 and 63 are aligned.

It wall of course be realised that while the above has been given by way of illustrative example of this invention, all such and other modifications and variations thereto as would be apparent to persons skilled in the art are deemed to fall within the broad scope and ambit of this invention as is defined in the appended claims.

The claims defining this invention are as follows:

1. A test sampling apparatus, comprising:

cutting means adapted for cutting a test sample from a piece of card;

a cut test sample produced by said cutting means;

receiving means for resiliently holding said cut test sample;

transportation means for delivering said cut test sample being held by said receiving means from said cutting means to a remote test container; and, discharge means adapted for discharging said test sample from said receiving means into said test container.

2. The test sampling apparatus as claimed in claim 1, wherein said receiving means comprises a receiving head having a recess which is adapted for resiliently holding said cut test sample when located within said recess, said receiving head being formed of a resilient material and wherein said recess includes a resilient inner boundary having selected transverse dimensions which are smaller than corresponding transverse dimensions of said cut test sample to be received therein.

3. The test sampling apparatus as claimed in claim 2, wherein said cutting means includes a punch and die set for cutting a test sample from a piece of card and wherein there is also provided location means for locating said receiving head relative to said punching means so that said recess is operatively aligned with said punching means for receiving a struck test sample.

4. The test sampling apparatus as claimed in claim 3, wherein said recess is formed by molding said receiving head about a corresponding pin.

5. The test sampling apparatus as claimed in claim 3, wherein said cutting means comprises a plurality of punch and die sets and receiving means includes a plurality of corresponding recesses for simultaneously receiving respective cut test samples struck from said plurality of punch and die sets and wherein said discharge means is operable for discharging a retained article from each said recess.

6. The test sampling apparatus as claimed in claim 3, wherein said punch is adapted for entering said recess for expanding an innermost boundary thereof and simultaneously advancing the cut test sample into said recess so that said innermost boundary will contract upon withdrawal of said punch from said recess and clamp about the cut test sample, wherein said punch having selected transverse dimensions which are larger than corresponding transverse dimensions of said innermost boundary.

7. The test sampling apparatus as claimed in claim 6, wherein said discharge means includes a plunger supported for movement into said recess for displacing the cut test sample, which is retained resiliently within said recess, from said recess and wherein said receiving head is supported by said transportation means for selective linear movement about X, Y and Z axes.

8. The test sampling apparatus as claimed in claim 2, wherein said resilient material is a polyurethane having a 90 Shore A durometer hardness.

9. The test sampling apparatus as claimed in claim 2, wherein said discharge means includes a plunger supported for movement into said recess for displacing the test sample from said recess and wherein said receiving head is supported by said transportation means for selective linear movement about X, Y and Z axes.

10. The test sampling apparatus as claimed in claim 2, wherein said punch is adapted for entering said recess for expanding said innermost boundary thereof and simultaneously advancing the cut test sample into said recess so that said innermost boundary will contract upon withdrawal of said punch from said recess and clamp about the cut test sample, wherein said punch having selected transverse dimensions which are larger than corresponding transverse dimensions of said innermost boundary.

11. A test sampling apparatus, comprising:

production means which comprises a punch and a die set for cutting a test sample from a piece of card;

receiving means for resiliently holding said cut test sample, said receiving means comprises a receiving head having a recess which is adapted for resiliently holding said cut test sample when located within said recess, said receiving head being formed of resilient material and wherein said recess includes a resilient inner boundary having selected transverse dimensions which are smaller than corresponding transverse dimensions of said cut test samples to be received therein;

location means for locating said receiving head relative to said production means so that said recess is operatively aligned with said punch and wherein said punch is adapted for entering said recess so as to expand said innermost boundary thereof and simultaneously deposit the cut test sample into said recess and so that said innermost boundary will contract upon withdrawal of said punch From said recess and clamp about the cut test sample, said punch having selected transverse dimensions which are larger than corresponding transverse dimensions of said innermost boundary;

transportation means for delivering said cut test samples held by said receiving means from said production means to a remote test container; and, discharge means adapted for discharging said test sample from said receiving means into said test container.

12. The test sampling apparatus as claimed in claim 11, wherein said discharge means includes a plunger supported for movement into said recess for displacing the cut test sample from said recess and wherein said receiving head is supported by said transportation means for selective linear movement about X, Y and Z axes.

13. The test sampling apparatus as claimed in claim 12, wherein said recess is formed by molding said receiving head about a corresponding plunger.

14. The test sampling apparatus as claimed in claim 11, wherein said resilient material is a polyurethane having a 90 Shore A durometer hardness.

15. The test sampling apparatus as claimed in claim 11, wherein said production means comprises a plurality of punch and die sets and said receiving means includes a plurality of corresponding recesses for simultaneously receiving respective cut test samples struck from said plurality of punch and die sets and wherein said discharge means is operable for discharging a refrained article from each said recess.

* * * * *